(12) United States Patent
Ashton et al.

(10) Patent No.: US 8,070,738 B2
(45) Date of Patent: Dec. 6, 2011

(54) PANT-LIKE DISPOSABLE GARMENT HAVING IMPROVED FASTENER SYSTEMS

(75) Inventors: Gregory Ashton, Cincinnati, OH (US); Michael Charles Raufman, Liberty Township, OH (US); Frederick Michael Langdon, Cincinnati, OH (US); Donald Louis Zgoda, West Chester, OH (US); Mark James Kline, Okeana, OH (US); Robin Lynn McKiernan, Mason, OH (US); Mary Lee Amirpour, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 515 days.

(21) Appl. No.: 11/045,654

(22) Filed: Jan. 28, 2005

(65) Prior Publication Data

US 2005/0177127 A1    Aug. 11, 2005

Related U.S. Application Data

(60) Provisional application No. 60/542,453, filed on Feb. 6, 2004.

(51) Int. Cl.
*A61F 13/15* (2006.01)

(52) U.S. Cl. .......................... 604/389; 604/391

(58) Field of Classification Search .................. 604/389, 604/391
See application file for complete search history.

(56) References Cited

U.S. PATENT DOCUMENTS

| | | | |
|---|---|---|---|
| 3,860,003 A | 1/1975 | Buell | |
| 4,005,713 A * | 2/1977 | Mesek | 604/378 |
| 4,523,333 A * | 6/1985 | Spangler | 2/49.3 |
| 4,610,678 A | 9/1986 | Weisman et al. | |
| 4,673,402 A | 6/1987 | Weisman et al. | |
| 4,695,278 A | 9/1987 | Lawson | |
| 4,795,454 A | 1/1989 | Dragoo | |
| 4,808,178 A | 2/1989 | Aziz et al. | |
| 4,834,733 A * | 5/1989 | Huntoon et al. | 604/361 |
| 4,834,735 A | 5/1989 | Alemany et al. | |
| 4,850,992 A * | 7/1989 | Amaral et al. | 604/389 |
| 4,888,231 A | 12/1989 | Angstadt | |
| 4,892,536 A | 1/1990 | DesMarais et al. | |
| 4,909,803 A | 3/1990 | Aziz et al. | |
| 4,990,147 A | 2/1991 | Freeland | |
| 5,037,416 A | 8/1991 | Allen et al. | |

(Continued)

FOREIGN PATENT DOCUMENTS

JP    63-012703    1/1988

(Continued)

*Primary Examiner* — Loan Thanh
*Assistant Examiner* — Lynne Anderson
(74) *Attorney, Agent, or Firm* — Charles R. Matson; Matthew P. Fitzpatrick

(57) ABSTRACT

Disposable pant like garments are disclosed. Pant like garments of the present invention generally comprise a main absorbent portion and a pair of side portions. One or more sections of the pant-like garments are provided with one or more cohesive areas which allow for cohesive fastening and refastening of portions of the garment. The cohesives chosen may have the same properties or may be of the selective adhesive type. Pant like garments may be provided with cohesive fasteners and not other types of refastening means. In other variations, cohesive fasteners may be supplemented with one or more frangible bonds. Also disclosed are side portions having cohesive areas which may be converted in use from an abutting facing relationship to an overlapping facing relationship. Multiple cohesive areas of varying types for providing differential bond properties during use are also disclosed.

9 Claims, 6 Drawing Sheets

U.S. PATENT DOCUMENTS

| | | |
|---|---|---|
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,260,345 A | 11/1993 | DesMarais et al. |
| 5,269,775 A | 12/1993 | Freeland et al. |
| 5,342,338 A | 8/1994 | Roe |
| 5,378,536 A | 1/1995 | Miller et al. |
| 5,387,207 A | 2/1995 | Dyer et al. |
| 5,397,316 A | 3/1995 | Lavon et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,625,222 A | 4/1997 | Yoneda et al. |
| H01674 H * | 8/1997 | Ames et al. .................. 604/389 |
| 5,807,368 A | 9/1998 | Helmer |
| 5,865,823 A | 2/1999 | Curro |
| 6,004,306 A | 12/1999 | Robles et al. |
| 6,287,287 B1 | 9/2001 | Elsberg |
| 6,352,528 B1 * | 3/2002 | Weber et al. ............. 604/385.03 |
| 6,428,526 B1 | 8/2002 | Heindel et al. |
| 6,552,245 B1 * | 4/2003 | Roessler et al. .............. 604/367 |
| 7,252,658 B2 * | 8/2007 | Sayama ........................ 604/396 |
| 2002/0099353 A1 | 7/2002 | Olson |
| 2003/0125702 A1 * | 7/2003 | Couture-Dorschner et al. ............................ 604/387 |

FOREIGN PATENT DOCUMENTS

| | | |
|---|---|---|
| JP | S64-45105 | 3/1989 |
| JP | H2-082974 | 3/1990 |
| WO | WO 95/16746 A1 | 6/1995 |
| WO | WO 95/27463 | 10/1995 |
| WO | WO 00/37016 A1 | 6/2000 |
| WO | WO 03/003963 | 1/2003 |
| WO | WO 03/045292 | 6/2003 |

* cited by examiner

PANT-LIKE DISPOSABLE GARMENT HAVING IMPROVED FASTENER SYSTEMS

FIELD OF THE INVENTION

The present invention relates to disposable absorbent articles and in particular disposable pant-like garments. More particularly, the present invention relates to a pre-fastened disposable pant like garment having improved fastener systems which provide adjustable, versatile, and refastenable, disposable products.

BACKGROUND OF THE INVENTION

Absorbent articles such as disposable diapers for infants and small children and adult incontinence products have long been known in the art. These articles are designed to absorb and contain body exudates such as urine and fecal matter. Ideally these products fit snugly and prevent leakage of exudates.

Typically, conventional diaper products for infants and small children have included a front waist portion, and a rear waist portion which are releasably connected about the hips of the wearer during use by fasteners such as adhesive tape fasteners or hook and loop type fasteners. Commonly such diapers were put on by laying the baby on its back, positioning the diaper between the baby's legs and fastening the fasteners about the waist.

More recently, there have been several prior art disposable absorbent articles of the so called "pants" type. These are articles designed to absorb and contain body exudates which are typically in a closed waist configuration and which are designed to be pulled up over the hips of the wearer into position around the waist and between the legs. This pulling up of such articles may be accomplished by a caregiver, by the wearer (such as a child) alone, or by the wearer with assistance from a caregiver. Typically, such pants type articles have a stretchable portion, such as a stretchable side area which expands to allows the article to be pulled over the hips and then retracts somewhat to provide a conforming fit of the article. Often such pants type articles are provided with a seamed area, such as seamed sides. The seams of such articles may be broken, such as by tearing, for removal of the article. A variation of the pants type articles are absorbent articles which are provided in a closed waist (or "pants") configuration and which can be pulled over the hips of the wearer into place about the waist. These articles are also provided, however, with a refastenable seamed area, such as refastenable side seams. A hook and loop fastener is one example of a refastenable seam which is known in the art used in conjunction with a pants type absorbent article for babies or young children.

U.S. Pat. No. 6,428,526, although not the first to do so, describes a pant like garment having pre-fastened hook and loop type fasteners at the side of the article. PCT Patent application WO 00/37016 discloses articles with primary and secondary fasteners where at least one of the fasteners are mechanical in nature. U.S. Pat. No. 6,287,287 discloses a refastenable primary fastener with passive side bonds located inwardly of said primary fasteners. The primary fasteners are mechanical in nature.

While some pants type absorbent articles with refastenable features have enjoyed some commercial success, use of currently available diaper fastening systems has drawbacks in this context. For example, the use of adhesives as part of a diaper fastening system has the drawbacks that adhesive may stick to itself or stick to portions of the article where such sticking is not desired. Other locations of undesired sticking may include skin, hair, etc. Mechanical fasteners, such as a hook and loop fasteners also have drawbacks. For example, hook type fasteners also may have a tendency to attach to undesired locations such as clothing, carpet, or the wearer (even if no sticking takes place, hooks may irritate the wearer's skin). Additionally, hooks and loops may prove challenging to integrate into a pant form with appropriate peel forces. If peel forces are too low, then children may have a tendency to remove the absorbent article when such removal is undesired. Other potential drawback of conventional mechanical fasteners is that many require an area without stretch properties in the overall article. This creates somewhat of a design paradox if stretch is generally desired in the side area of the product, but the mechanical fastener (such as a hook and loop) which is also to be placed on the side must be placed in an area without stretch properties. The compromise made is typically to limit the size of the hook and loop fastening area which results in a lack of versatility of the product and can lead to compromise on either the desired fastener strength properties or the stretch properties of the side portion of the article.

Another problem often associated with mechanical type fasteners is that they can tend to become damaged during the high speed operations required for commercially viable manufacture of pant like disposable garments. For example, hooks tend to get damaged during manufacture, and other mechanical type fasteners such as buttons, tab and slots, or the like can also become damaged, torn, or otherwise impacted by the challenges of high speed handling.

The articles of the present invention provide pants type disposable garments which overcome the drawbacks associated with mechanical type fasteners and also avoiding the problems seen with conventional adhesive fasteners. By employing various types of selective adhesive fastening techniques either alone or in combination with fastening techniques, the articles described herein offer improved versatility, fit, refastening performance over those previously known in the art. These and other advantages of the articles of the present invention will become apparent in light of the description below.

SUMMARY OF THE INVENTION

The present invention is directed to a disposable pant like garment. The disposable pant like garment may comprise a main absorbent portion and a pair of side portions. The main absorbent portion may comprise at least a liquid permeable topsheet, a liquid impermeable backsheet, and an absorbent core disposed therebetween. Additionally, the main absorbent portion may have a front waist region, a rear waist region and a crotch region between and connecting the front and rear waist regions. The side portions of the garment may each comprise a front side portion disposed generally transversely from the front waist region and a corresponding rear side portion disposed generally transversely from the rear waist region. The disposable pant like garment may further comprise a cohesive fastening system. The cohesive fastening system may comprise an engaging member having an engaging surface and a receiving member having a receiving surface. The engaging surface may include a cohesive substance disposed on the engaging surface which engages with the cohesive on the receiving surface to form a closed pant like garment having a refastenable connection. The cohesive substances may be the only refastening means provided to the side portions.

The disposable pant like garment may be packaged in a closed configuration.

The cohesive substance disposed on the engaging surface may be the same as the receiving cohesive substance disposed on the receiving surface. The cohesive substance disposed on the engaging surface may be different from the receiving cohesive substance disposed on the receiving surface.

The cohesive receiving substance may be disposed on substantially the entirety of said front side portion.

The disposable pant like garment may comprise a main absorbent portion and a pair of side portions. The main absorbent portion may comprise at least a liquid permeable topsheet, a liquid impermeable backsheet, and an absorbent core disposed therebetween. The main absorbent portion may have a front waist region, a rear waist region and a crotch region between and connecting said front and said rear waist regions. The side portions may each comprise a front side portion disposed generally transversely from said front waist region and a corresponding rear side portion disposed generally transversely from said rear waist region. Each of said front side portions may include a cohesive engaging area and each of said rear side portions may include a cohesive receiving area. Each of said front side portions may be frangibly bonded to said corresponding rear side portion in an abutting facing relationship over at least a portion of their surfaces. Upon breaking of said frangible bonds, each front side portion and its corresponding rear side portions may be refastenably joined together at the cohesive engaging and cohesive receiving areas in an overlapping configuration over at least a portion of their respective surfaces.

The frangible bonds may be thermal bonds. The frangible bonds may be pressure bonds.

The disposable pant like garment may comprise a main absorbent portion and a pair of side portions. The main absorbent portion may comprise at least a liquid permeable topsheet, a liquid impermeable backsheet, and an absorbent core disposed therebetween. The main absorbent portion may have a front waist region, a rear waist region and a crotch region between and connecting said front and said rear waist regions. The side portions may each comprise front side portion disposed generally transversely from said front waist region and a corresponding rear side portion disposed generally transversely from said rear waist region. Each said front side portion may comprise an area containing a cohesive of type A and a second distinct area containing a cohesive of type B. Each said corresponding rear side portion may comprise an area containing a cohesive of type A and a second distinct area containing a cohesive of type B. Each of said cohesive type A and cohesive type B on said front side portions may be capable of forming a cohesive bond with either cohesive type A or cohesive type B on said corresponding rear side portion. At least one bond property of the resulting cohesive bond may vary depending on whether said cohesive bond is formed between cohesives of the same type or cohesives of differing types.

The disposable pant like garment may comprise a main absorbent portion and a pair of side portions. The main absorbent portion may comprise at least a liquid permeable topsheet, a liquid impermeable backsheet, and an absorbent core disposed therebetween. The main absorbent portion may have a front waist region, a rear waist region and a crotch region between and connecting said front and said rear waist regions. The side portions may each comprise a front side portion disposed generally transversely from said front waist region and a corresponding rear side portion disposed generally transversely from said rear waist region. Each of said front side portions may include a first cohesive area and each of said rear side portions may include a second cohesive area. Each of said first cohesive areas and said second cohesive areas may provide each front side portion fastening and refastening capability to said corresponding rear side portion. At least a portion of said first cohesive area and said second cohesive areas may be locations of extensibility of said side portions when said front and said corresponding rear side portions are refastenably engaged.

DETAILED DESCRIPTION OF THE INVENTION

Figure 1:
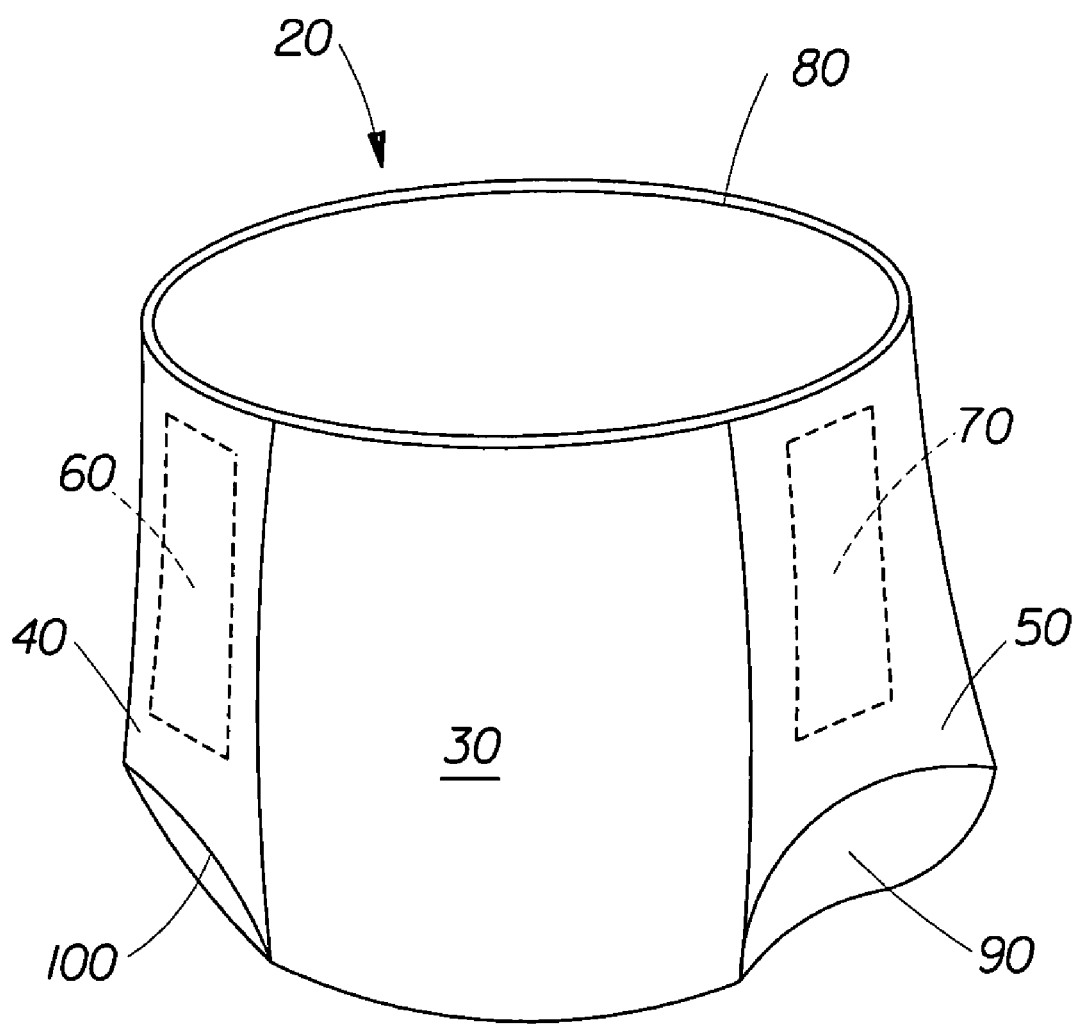
FIG. 1 is a perspective view of a disposable pant like garment according to the present invention.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane" refers to the plane congruent with the longitudinal and transverse directions.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "pant-like" refers to an article configured such that it has a waist opening and a pair of leg openings. This configuration may be permanent as in the case of conventional underwear, or may be temporary as in the case of a training pant with openable seams for removal. Additionally, absorbent articles can be constructed with refastenable features allowing the article to have both a pant-like configuration and one or more configurations which are open or not pant like.

As used herein the term "refastenable" refers to the attachment of two or more elements or portions of elements together in a manner in which they can be separated and re-attached successively without substantial degradation of fastener performance or damage to surrounding components of the article which would impair its continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening or tack may be reduced significantly from fastening to refastening in absolute terms, but that such reduction is not "substantial degradation" of fastener performance if the resulting refastened strength is sufficient for its purpose of use in a disposable absorbent article.

As used herein "frangible bond" refers to attachment of two or more elements or portions of elements together in which they may be separated during normal use, but upon separation cannot be re-attached without substantial degradation of fastener performance. A frangible bond is generally designed to be broken by the consumer at some point during normal use of the article. The breaking of this bond may be optional depending on desired use, or it may occur in substantially all use occasions.

As used herein "permanent bond" refers to attachment of two or more elements or portions of elements together in a manner in which they are not intended to be separated during normal use of the article. Separation of such a permanent bond results in degradation of not only the attachment, but of at least portions of the article and the performance of the article for its intended use is compromised upon breaking of a permanent bond.

As used herein, the term "impermeable" generally refers to articles and/or elements that are not penetrative by fluid through the entire Z-directional thickness of the article under pressure of 0.14 lb/in$^2$ or less. The impermeable article or element also may not be penetrative by fluid under pressures of 0.5 lb/in$^2$ or less. The impermeable article or element may also not be penetrable by fluid under pressures of 1.0 lb/in$^2$ or less.

As used herein the term "mechanical fastener" refers to a fastening system or mechanism relying on physical restraint or engagement of portions of the fastener for operation. Examples of mechanical fasteners are hook and loops, buttons, snaps, tab and slots, zippers, and tongue and groove fasteners.

As used herein, the term "adhesive" or "typical adhesive" are interchangeable and refer to a material which demonstrates connection when applied to another material generally (e.g. material is not specially selected). Adhesive materials connect to other materials generally and no particularly selected properties of the other material are necessary for such tack to be demonstrated. Generally, typical adhesive materials used in disposable absorbent articles demonstrate such tack either at certain temperatures (such as a hot melt adhesive) or under pressure (a pressure sensitive adhesive).

As used herein, the term "cohesive" refers to a material which demonstrates surface interaction (in terms of connection of one surface to another) when applied to a specially selected material. An A-A type cohesive material will fasten or form a connection primarily to itself or to similarly structured materials. Generally, such materials are substantially non-tacky (such as to skin) at room temperature even under some pressure. An A-B type selective adhesive material demonstrates surface interaction properties where material A will stick to different material B. However, A may also attach to A and B may attach to B. An A-B type cohesive system could also exist where type A material may attach to material of type A or type B, but the B type material will not attach to itself or other materials other than A. For purposes of the present specification, the term cohesive will include materials which are sometimes referred to as "selectively adhesive" or "selective adhesive" materials. Materials which are designed to receive (i.e. allow the surface interaction) with a particular cohesive material, but which themselves will not connect with any other materials (or itself) are still considered "cohesive materials" within the meaning of this specification when they act as the target surface for a specific cohesive engaging material.

As used herein the term "extensible" refers to materials which elongate or increase in at least one dimension when subject to an external pulling force.

As used herein the terms "stretchable" or "elastic" are intended to be interchangeable and refer to materials which are extensible and which also return to substantially their original dimensions when the external pulling force is removed. It will be appreciated that the terms stretchable and elastic include the term extensible as each term is used herein.

The present invention relates generally to disposable pant like garments such as diapers. In particular, the pant like garments of the present invention may be of the "refastenable" type. In other words, the article may be provided to the consumer in either a closed or "pant like" configuration (i.e. the article has a complete waist encircling opening) or the article may be provided in an "open" configuration (i.e. the waist opening is not complete in this configuration. In either case, the user may make use of the refastenability feature to open the waist from a closed to open configuration or to close it from an open to closed configuration. Preferably, the refastenable feature allows for such opening and closing of a portion of the article multiple times during the life cycle of the disposable pant like garment.

FIG. 1 shows an example of a basic pant like garment of the present invention. The garment 20 shown in FIG. 1 generally comprises a main absorbent portion 30 and a pair of side areas 40 and 50. The main absorbent portion 30 taken in combination with the side portions 40 and 50 generally define a waist opening 80 and a pair of leg openings 90 and 100. Each of the side areas 40 and 50 may be stretchable, including elastically stretchable. Additionally, each of the side areas 40 and 50 may be provided with a refastenability feature allowing the side areas 40 and 50 to be opened and re-closed along either or both of side attachment areas 60 and 70. As shown in FIG. 1 when the side areas 40 and 50 are each closed along respective side attachment areas 60 and 70, the waist opening 80 is complete and the garment 20 is said to be in a closed or pant-like configuration.

Figure 2:
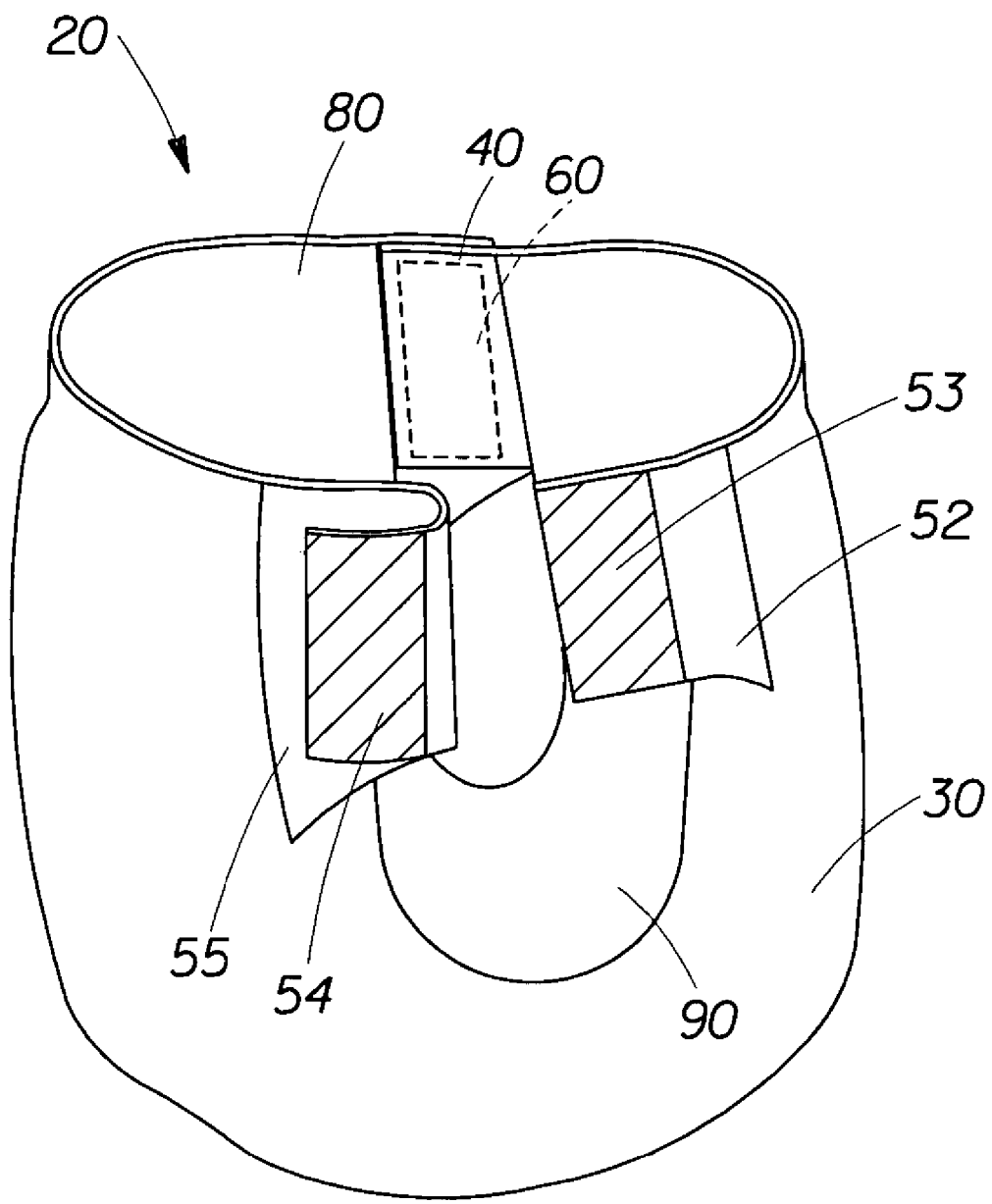
FIG. 2 is a perspective view of a disposable pant like garment according to the present invention showing its left side portion in an open configuration.

FIG. 2 shows the garment of FIG. 1 in which the right side attachment area has been opened. When one or both of the side areas 50 and 60 is so opened, the garment 20 is said to be an open configuration. The respective side portions 50 and 60 of the garment 20 may be either separately attached to the main absorbent portion 30 or may be made integrally with the main absorbent portion 30.

Figure 3:
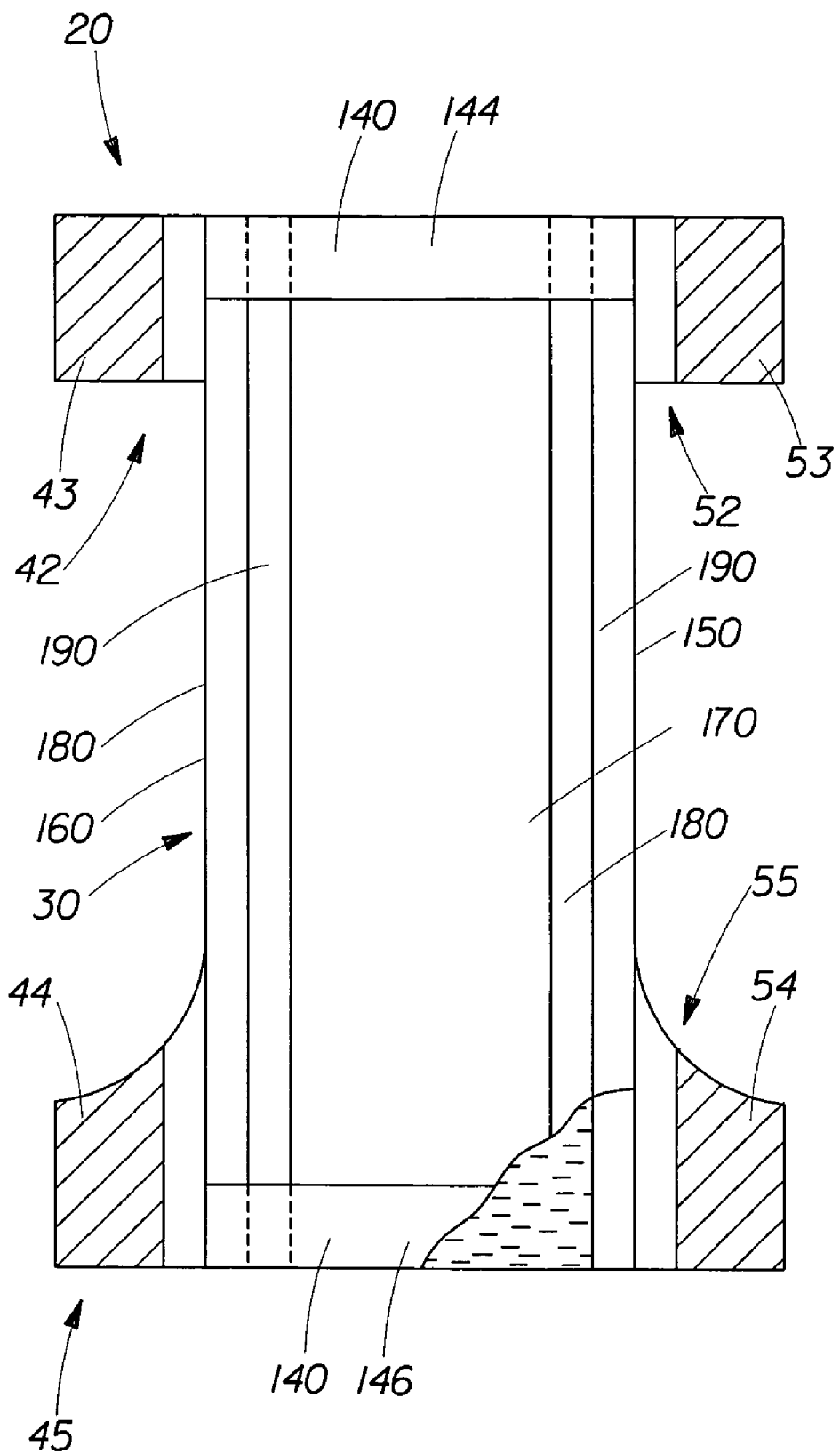
FIG. 3 is a plan view of a disposable pant like garment according to the present invention laid flat in its uncontracted state.

FIG. 3 shows the garment of FIG. 1 and FIG. 2 laid flat in its open uncontracted state. Garment 20 is generally composed of a main absorbent portion 30 and side areas. As shown in FIG. 3, when the garment 20 is open and unfolded, the side areas are separated into front side portions 42 and 45, and rear side portions 52 and 55.

The main absorbent portion 30 generally includes a pair of longitudinal edges, left edge 160, and right edge 150. The main absorbent portion also includes a pair of transverse ends, front waist region 144, and rear waist region 146. These waist regions may be provided with elastic gathering features, padding features, containment features, or any other features typically provided in the waist regions of disposable absorbent articles of this type, a wide variety of which are known in the art. An example of such a feature is shown in FIG. 3 as waist feature 140. The area of the main absorbent portion 30 between the described waist regions is typically referred to as the crotch region 170. The crotch region 170 is that portion of the garment 20 which, when the garment 20 is worn, is generally positioned between the legs of the wearer. As with the waist regions, the crotch region 170 may be provided with any of the features typically provided on disposable absorbent garments of this type. Examples of such features typically employed in the art are leg elastic, barrier containment structures, graphics, notches for fit or appearance, etc.

The main absorbent portion 30 of the garment 20 typically comprises at least a liquid pervious topsheet 130, a liquid impervious backsheet 120, and at least a portion of an absorbent core 110 encased between the topsheet 130 and the backsheet 120. For unitary absorbent articles, this basic assembly comprises the main structure of the diaper with other features added to form the main absorbent portion 30 and ultimately the garment 20 as a whole. While the topsheet 130, the backsheet 120, and the absorbent core 110 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 130 may be fully or partially elasticized or may be foreshortened so as to provide a void space between the topsheet 130 and the core 110. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The absorbent core 110 may comprise any absorbent material that is generally compressible, conformable, non-irritating to the wearer's skin, and capable of absorbing and retaining liquids such as urine and other certain body exudates. The absorbent core 110 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; superabsorbent fibers; or any other known absorbent material or combinations of materials.

Exemplary absorbent structures for use as the absorbent cores (either single layer, or multi layer composite structures) are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

The backsheet 120 is generally that portion of the garment 20 positioned adjacent the garment-facing surface of the absorbent core 110. Backsheet 120 prevents the exudates absorbed and contained therein from soiling articles that may contact the garment 20, such as bed sheets and undergarments. In preferred embodiments, the backsheet 120 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the garment 20 while still preventing exudates from passing through the backsheet 120. Exemplary breathable materials may include materials such as woven webs, non-woven webs, composite materials such as film-coated non-woven webs, and microporous films such as manufactured by Mitsui Toatsu Co., of Japan under the designation ESPOIR NO and by Tredegar Industries under the designation EXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

Backsheet 120 may also consist of more than one layer wherein a backsheet outer layer (often referred to simply as the backsheet) may be made of a soft, non-woven material and a backsheet inner layer may be made of a substantially impermeable film. Even if not referred to as the backsheet, pant like garments desirably have an outer cover layer of soft material. This layer may extend beyond the edges of the main absorbent portion 30 (e.g. it may also extend into and cover the side areas) or it may be coterminous with other layers of the main absorbent portion 30. Adhesive, or any other suitable material or method, may be used to join backsheet layers together. While a variety of backsheet configurations are contemplated herein, it would be obvious to those skilled in the art that various other changes and modifications can be made without departing from the spirit and scope of the invention.

The garment 20 may also include such other features as are known in the art including cuffs, waist cap features, elastics and the like to provide better fit, containment and aesthetic characteristics. Such additional features are well known in the art and are described in U.S. Pat. No. 3,860,003; and U.S. Pat. No. 5,151,092, which are incorporated by reference herein.

For example, garment 20 may include barrier cuffs 180 which provide improved containment of liquids and other body exudates. Barrier cuffs 180 may also be referred to as barrier leg cuffs, inner leg cuffs, containment flaps, or "stand-up" elasticized flaps. U.S. Pat. Nos. 4,808,178 and 4,909,803 issued to Aziz et al. on Feb. 28, 1989 and Mar. 20, 1990, respectively, describe disposable diapers having "stand-up" elasticized flaps that improve the containment of the leg regions.

Additionally, garment 20 may include gasketing cuffs 190 which also provide improved containment of liquids and other body exudates. Gasketing cuffs 190 may also be referred to as outer leg cuff, leg bands, side flaps, leg cuffs or elastic cuffs. U.S. Pat. No. 3,860,003 describes a disposable diaper which provides a contractible leg opening having a side flap and one or more elastic members to provide an elasticized leg cuff.

Barrier cuff 180 and gasketing cuff 190 may both be provided by way of a dual cuff, as exampled in U.S. Pat. Nos. 4,695,278 and 4,795,454 issued to Lawson on Sep. 22, 1987 and to Dragoo on Jan. 3, 1989, respectively. Any of the elastic materials known in the art typically employed in such cuff structures are suitable for use in garments of the present invention is cuff structures are employed. Cuffs may be joined to the main absorbent portion 30 using any suitable means known in the art.

As shown in FIGS. 1-3, in addition to the main absorbent portion 30, the garment 20 generally comprises a pair of side areas such as left side area 40 and right side area 50. As previously noted the side areas may be integral with the main absorbent portion 30 (that is they may be continuous extensions of one or more of the layers of the main absorbent portion 30) or they may be separately attached to the main absorbent portion 30. Alternatively, the side areas may be made of multiple components or layers some of which are discrete (either attached separately to the main absorbent portion or separated therefrom by a gap) and some of which are continuous. An example of this type of construction is a garment provided with an outer nonwoven cover which completely covers all areas of the garment 20 including the side areas 40 and 50 and the main absorbent portion 30.

The side areas 40 and 50 together with the main absorbent portion form a pant like garment 20 having a waist opening 80 and a pair of leg openings 90 and 100, when said pant like garment is in a closed configuration. As shown in FIGS. 1-3 the front side portions are disposed generally transversely outward from said longitudinal edges 150 and 160 of said main absorbent portion 30 at or near the front waist region 144. Similarly the rear side portions 45 and 55 are disposed generally transversely outward from said longitudinal edges 150 and 160 of said main absorbent portion 30 at or near the rear waist region 146. In this manner the respective waist regions together with the side portions (both front and rear) form a complete waist opening when the front and rear waist portions are joined such as at attachment areas 60 and 70. Similarly, the main absorbent portion 30 and the side portions in combination also form leg openings 90 and 100 in a similar manner.

Preferably, the side areas 40 and 50 may be extensible or more preferably elastic. The side areas may be made extensible or elastic by any of a variety of techniques known in the art. For example, an elastic side area can be made by sandwiching elastic strands or films between facing layers of cover material, such as a non-woven material. Typically, in such a construction the elastic stands are attached to the facing layers while in a stretched configuration. After attachment, the strands are allowed to relax thereby gathering the facing layers and creating an elastic laminate. Alternatively, elastic strands or film can be attached to one or more facing layers in either a relaxed configuration or partially stretched configuration. The resulting laminate can be made stretchable (or more stretchable over a further range) by subjecting the laminate to an elongation process which elongates the facing layers permanently, but the elastic stands or layer only temporarily. Such processes are known in the art as "zero strain" stretch laminates, and the elongation of such laminates may be accomplished with suitable means such as rollers, engaging teeth, or the like. Examples of zero strain activation processing and formations of resulting stretchable laminates are described in U.S. Pat. No. 5,167,897 issued to Weber et al. and U.S. Pat. No. 5,156,793 issued to Buell et al.

As shown in FIGS. 1 and 2, the side areas may be provided with attachment areas for attaching the front side areas to the rear side areas. Examples of such attachment areas are left side attachment are 60 and right side attachment area 70 shown in FIG. 1. As shown in FIGS. 1-3, these attachment areas may be located approximately midway between the front and back portions of the respective side areas. However, this is not necessary and any location along the side area is acceptable to locate an attachment area.

In one embodiment of the present invention attachment areas seams such as left and right attachment areas 60 and 70 are created through the attachment of front and back portions of the side areas with a refastenable reclosure device. Other refastenable attachment areas other than in the side seam (in addition to or instead of such a side seam) are also possible. For example, such an area could be at the boundary between one or both of the side panels and the main absorbent portion. In one embodiment, such a refastenable device may be through use of cohesive materials. For example, FIG. 3 shows front and rear left side areas 42 and 45 provided with cohesive areas 43 and 44 over at least a portion of their respective surface areas. Similarly right side areas 52 and 55 are provided with cohesive areas 53 and 54. For ease of description, more details of the construction in FIG. 3 will be given with respect to the left side area. However, the same description may be applicable to side areas located on each side of the product.

FIG. 3 shows front side area 42 and rear side area 45 each provided with a cohesive area 43 and 44 respectively. The cohesive areas 43 and 44 may cover only a portion of the side areas as shown in FIG. 3, or they may be coextensive with each portion of the side area. Each of the front side area 42 and rear side areas 45 may be made out of a material which is manufactured so as to be both elastic and cohesive (e.g. the material may be extruded as strands of elastic cohesive material which is woven into a web or otherwise formed into an elastic cohesive web). In other variations, the side areas may be formed and a cohesive coating may be applied separately as desired to desired portions of the side areas. In the embodiment shown in FIG. 3, the cohesive area 43 is designed to have connection properties with cohesive area 44. The cohesive material used in cohesive area 43 may be the same or in the same class of materials as that used in 44 (a so called A-A cohesive relationship) or it may be a different material (an A-B cohesive relationship). In either case, it is desired that the cohesive material only connect or fasten (i.e. form a connection to) the intended target cohesive material and not to other materials generally.

In the embodiment shown in FIG. 3 the refastening capability of the side area consists of the cohesive areas 43 and 44. In this embodiment, no other refastening capability is needed or provided to the side areas. The cohesive material provided in the cohesive areas may be located on one or both facing surfaces (i.e. the body facing surface and the garment facing surface) of the respective side areas. If the cohesive material is located on only one of the facing surfaces, the material may be disposed on opposite facing surfaces on each of the front and rear side areas. In this manner, the resulting side areas when closed, can have an overlapping configuration. Because the cohesive material will connect or fasten to selective materials (referred to generically as other cohesive materials, whether the "target" or the engaging material) and not to other materials generally, the use of cohesive materials for refastening allows for disposition of cohesive materials on both sides of the respective side areas. This provides the advantage that during fastening or re-fastening, the consumer may overlap either portion of the side area with the other and still have a viable refastenable closure means. By contrast, most mechanical fastening systems (such as hook and loop systems) require that the complimentary components be mated in only one relationship to work properly. It may be desired, nevertheless, to place an engaging cohesive material and corresponding target receiving area on only one side of a portion of the article (such as opposite side panels). In this case, there will only be one overlapping configuration which will make a connection (e.g. front panel over back or back panel over front).

Because the cohesive material will only connect or fasten aggressively to selected target material (of either the same or complementing type), the size of each cohesive area may be larger than the space actually needed for overlap of the front and rear portions of the side areas. In other words, the size of cohesive areas such as cohesive area 43 and 44 need not be the same as the resulting attachment area 60 when the garment is closed into a pant like configuration. Indeed if the front and rear side portions are opened and re-fastened several times during use of the article, the amount of overlap and the resulting size of the attachment area thereby created may be varied each time if desired. In such a case any cohesive material on the remaining exposed (i.e. not overlapping) portions is not of concern since this cohesive material should not connect to skin, clothing, or other portions of the garment. By combining stretch properties with cohesive materials in the side areas, the refastening capability can also provide for size selection of the resulting waist opening.

A wide variety of cohesive materials may be used to form the cohesive refastenable features shown in FIG. 3. Ideally the resulting seam areas will demonstrate high resistance to shear forces in use, but significantly less resistance to peel forces in use. For example, the cohesive materials may be chosen to demonstrate resistance to shear forces greater than 10N, preferably greater than 30 N. Similarly the resistance to peel forces might range from about 0.5 N to about 25 N, or could range from about 0.5 N to about 15 N, and could range from about 0.7 N to about 10 N. The cohesive materials may be chosen such that the cohesive attachments areas may be detached and refastened at least about 3 times before product disposal.

Typically, many conventionally available cohesive materials are pressure sensitive. That is, the degree of fixation the materials demonstrate to the selected cohesive target increases with increased pressure with which the materials are pressed together. During initial formation of a pant like garment according to the present invention high pressure may be applied to create side seams between cohesive areas of respective side panels. In this manner the garment may be initially presented in a closed or pant like configuration. Because the side seams were formed using high pressure, a relatively small amount of overlap (as compared to overlap during refastening) may be required between the respective side areas to achieve sufficient strength of the side seam. Once the article is pulled over the hips of the wearer, the side seams may be re-adjusted and refastened with more overlap to achieve a more snug fit. This greater overlap also results in greater cohesive bond strength even though the pressure applied to the materials may be less than the pressure applied during initial formation of the pant like configuration. In such a manner the benefits of refastenability and adjustability of the waist opening are achieved in combination. This is particularly true if the side areas in which the cohesive areas are sited are elastic.

It will be readily appreciated by those of skill in the art that the overall dimensions of the disposable pant like garment 20 may vary depending on the intended size and age range of the wearer. For example, it may be desirable to provide pant like garments of the present invention in a variety of sizes to accommodate various toddler stages of development and to provide such products with features corresponding to one or more of such stages. The size of the side portions may vary and suitable sizes might range from about 2 cm to about 15 cm in length (in the longitudinal direction) and from about 12.7 cm to about 381 cm (measured in the transverse direction). Similarly, the size of the cohesive areas provided on the side areas may also vary. The cohesive areas may be coterminous with each of the side areas upon which they are disposed. Alternatively, the cohesive areas may occupy only a portion of the side areas on which they are disposed. In order to gain the benefits of both refastenability and adjustability, it may be desired to have cohesive areas on one or more side areas which are about 5 to about 60 mm or more in width or which are about 15 to about 20 mm in width.

Figure 4:
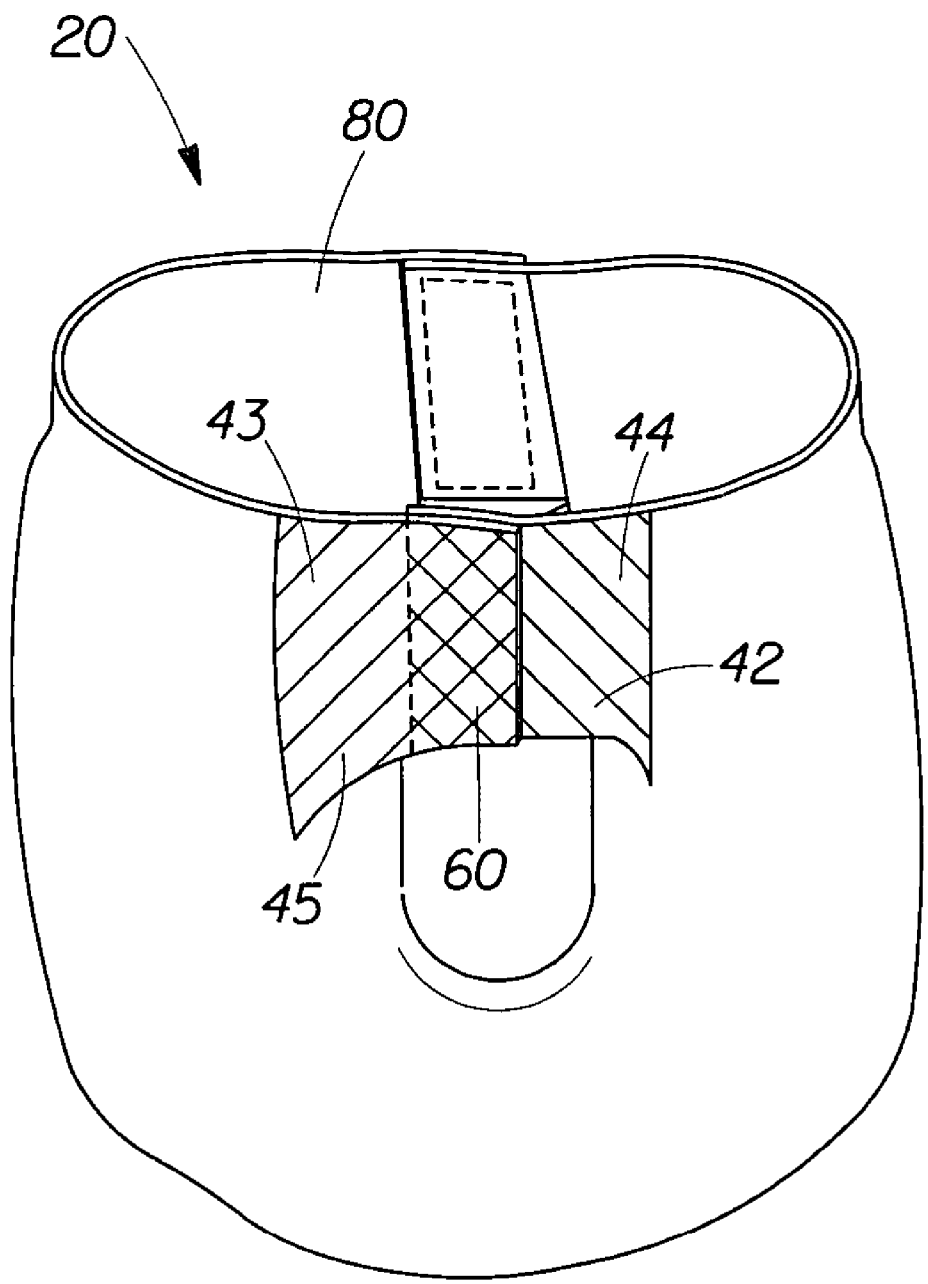
FIG. 4 is a perspective view of a disposable pant like garment according to the present invention showing an additional embodiment of the side area configuration.

In the embodiment shown in FIG. 3 the first cohesive area 43 disposed on front side portion 42 is coterminous in the longitudinal direction with the front side portion, but not in the transverse direction. Similarly, second cohesive area 44 disposed on rear side portion 45 is also coterminous in the longitudinal direction with the rear side portion, but not in the transverse direction. FIG. 4 shows a variation of a front side portion and a corresponding rear side portion of a garment 20 of the present invention in which each of first and second cohesive areas 43 and 44 are coterminous with front and corresponding rear side portions, respectively. In this particular case, the attachment area 60 is only a portion of the side areas and represents the portion over which the front side portion 42 and rear side portions 45 are overlapped for attachment to each other.

While advantages of the present invention have been described over the use of mechanical type fasteners in disposable pant like garments, there may be some circumstances in which additional advantages can be achieved by employing cohesive fasteners in combination with other attachment means. In particular, unique combinations of cohesive refastening areas in combination with frangible bond locations can afford even additional benefits over currently known disposable pant like garments.

Figure 5:
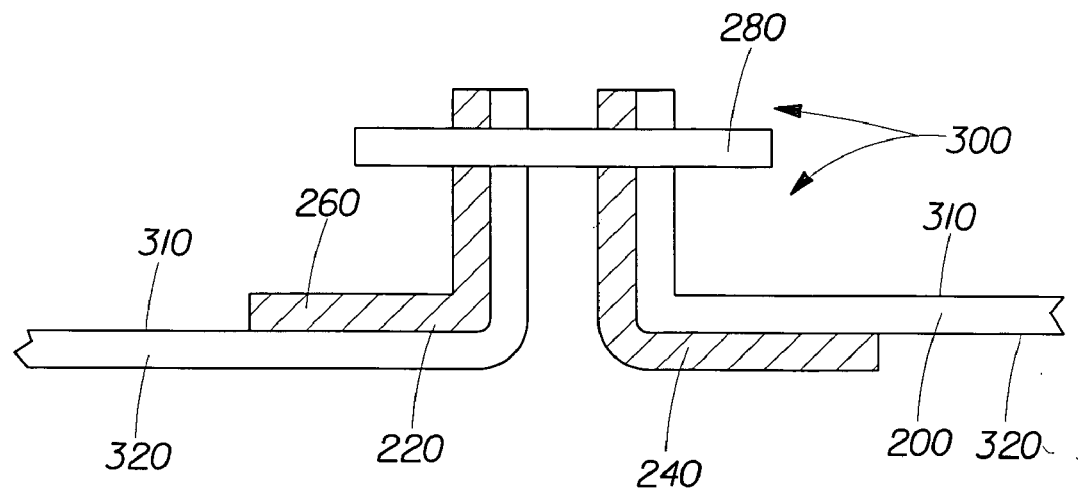
FIG. 5 shows one side portion of a garment of the present invention in which there is an abutting relationship between sections of the side portion.
Figure 6:
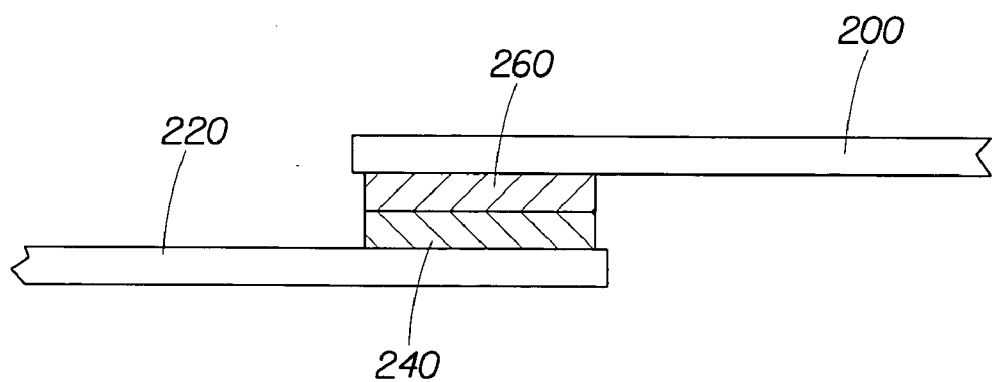
FIG. 6 shows one side portion of a garment of the present invention in which there is an overlapping relationship between sections of the side portion.

An example of an embodiment of this type is shown in FIGS. 5 and 6. FIG. 5 shows an example of how a front side portion 200 and a rear side portion 220 of such an embodiment might be configured. In the embodiment shown in FIG. 5 front side portion 200 has a first cohesive area 240 disposed on one of its surfaces. For example, if this front side portion is located on the left side of the complete pant like garment first cohesive area 240 might be on the body facing side of the front side portion. As previously noted, because the cohesive material will only connect to another designated cohesive area contact of the first cohesive area 240 with the skin is not of concern (provided that the cohesive material chosen of course, is not irritating and otherwise meets safety and regulatory requirements for use in articles of this type). The rear side portion 220 contains a second cohesive area 260 disposed on one of its surfaces. In the example shown in FIG. 5 the surface upon which second cohesive area 260 is disposed is opposite that of first cohesive area 240. Both cohesive areas may alternatively be disposed on the opposite facing surfaces of their respective side portions, or both may be on the same facing surface. Alternatively, both facing surfaces of each side portion may be provided with a cohesive area.

FIG. 5 also shows a frangible bond 280 joining the front side portion 200 and the rear side portion 220. Frangible bond may be of any suitable type such a pressure bond, a thermal bond, an adhesive bond, an ultrasonic bond, or any other type of bond which may be broken by a user or caregiver during normal use of the article. FIG. 5 shows the front side portion 200 and the rear side portion 220 are joined by frangible bond 280 in an abutting relationship over at least a portion of the surface of each of said front side portion 200 and said rear side portion 220. By an abutting relationship, it is meant that at least a portion of the same facing surface (i.e. body facing surface or garment facing surface of both the front side portion and the rear side portion are joining in a face to face relationship. An abutting relationship is distinguished from an overlapping relationship (shown in FIG. 6) which is a relationship in which face to face contact between the font side portion and rear side portion occurs on opposite facing surfaces of each portion (e.g. the body facing side of the front side portion is in face to face contact with a portion of the garment facing side of the rear side portion). The abutting relationship shown in FIG. 5 shows a section 300 of the body facing side 320 of front side portion 200 turned outwardly and placed in face to face contact with a section of the body facing side 320 of rear side portion 220. Alternatively, an abutting relationship can be created by face to face contact with at least sections of the garment facing surface 310 of each of the front side portions 200 and the rear side portion 220.

FIG. 6 represents a potential configuration of front side portion 200 and rear side portion 220 after frangible bond 280 has been broken and the cohesive areas are placed together to form a cohesive refastenable joining of the front and rear side portions. As shown in FIG. 6 first cohesive area 240 from front side portion may be placed in face to face relationship with second cohesive area 260 from rear side portion 220. Because these cohesive areas are disposed on opposite facing surfaces of their respective side sections, the resulting face to face contact is an area of overlapping configuration as described above. The ability for a user to make such conversion from an abutting relationship offers several advantages. Firstly, the manufacture of the article in the configuration shown in FIG. 5 with a frangible bond is readily accomplished with such an abutting relationship. Upon breaking of the frangible bond, if desired, the user may employ an overlapping relationship to take advantage of the cohesive bonds thereby formed. In the abutting relationship, the cohesive areas are not facing each other, thereby not creating a cohesive bond prior to the time such is needed or desired (e.g. after the frangible bond is broken). It is desirable that the cohesive attachment of front side portion 200 and rear side portion 220 as shown in FIG. 6 result in adjustable attachment. In other words the first cohesive area 240 and second cohesive area 260 may be positioned so that they line up completely, or only a portion of each cohesive area may be placed in contact with its complementing cohesive area. Particularly, if the size of each cohesive area is large in relationship to the side section as a whole, the entire cohesive areas are unlikely to be overlapped. The additional cohesive area provided allows for a range of adjustability of the overall side portion of the garment.

Figure 7:
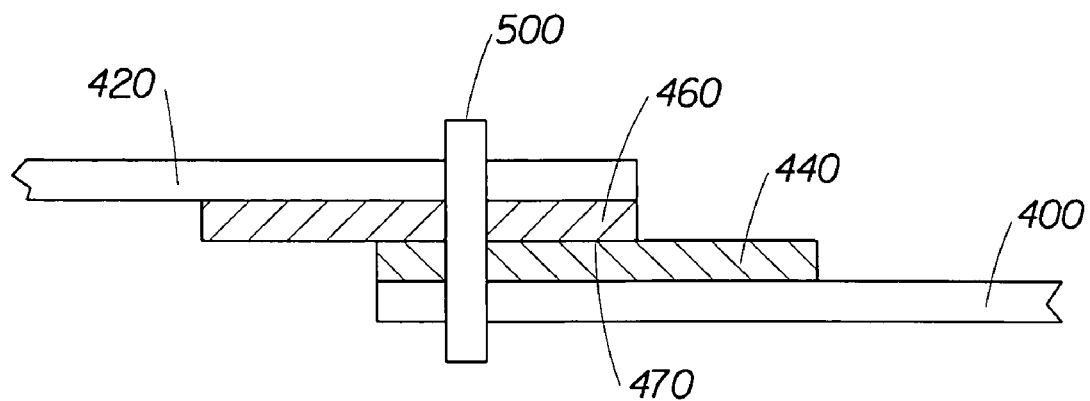
FIG. 7 shows a side portion of a garment of the present invention showing frangible bonding and cohesive bonding used in combination.

FIG. 7 shows another variation on the side portions of garments of the present invention. FIG. 7 shows a front side portion 400 and a rear side portion 420. The front side portion is provided with first cohesive area 440 and the rear side portion is provided with second cohesive area 460. First and second cohesive areas partially overlap in a face to face relationship to form a cohesively bonded attachment area 470. Such an attachment area could correspond to attachment area 70 shown in FIG. 1. FIG. 7 also shows a frangible supplemental bond such as pressure bond 500. Of course, this frangible bond may be of any of the types described above with respect to FIG. 5. In an article having the configuration shown in FIG. 7 both the frangible bond 500 and cohesive attachment area 470 might be engaged at the time the garment is packaged and provided to the consumer. The consumer may break one or both of these bonds and selectively refasten the cohesive attachment as desired.

Figure 8:
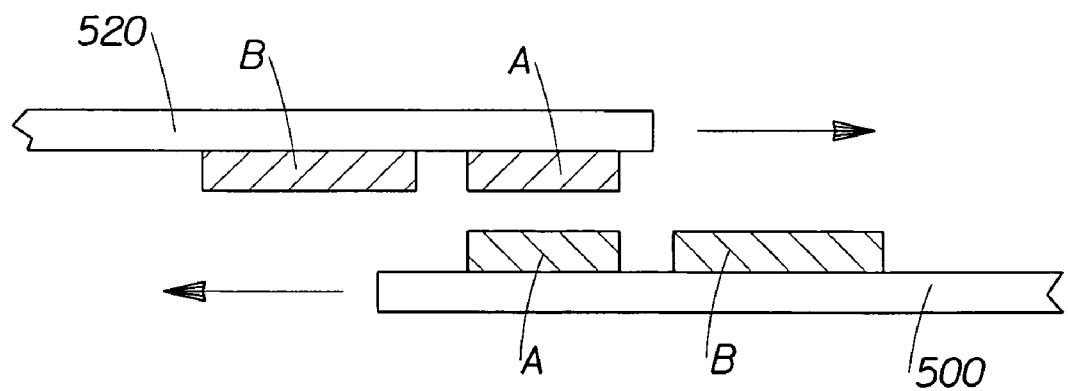
FIG. 8 shows a side portion of a garment of the present invention showing multiple cohesive zones of differing types allowing for different bonding properties.

FIG. 8 shows another aspect of the present invention in which multiple cohesive areas of different types are present on the front side portions and rear side portions. For example, as shown in FIG. 8 front side portion 500 may be provided with two or more cohesive areas such as cohesive area A and cohesive area B. Each of cohesive A and B is a different composition and is designed to form a cohesive bond with either cohesive material of the same type or of the other type. Rear side portion 520 also has cohesive area A and cohesive area B. In the configuration shown in FIG. 8 at least one cohesive area A is directly opposite another cohesive area A. If front side portion 500 and rear side portion 520 are elastic, they may be stretched in the direction of the arrows and refastened such that each cohesive area A overlaps each cohesive area B. In this embodiment each of cohesive A and cohesive B are selected and chosen so that at least one bond property changes depending on whether the resulting cohesive bonding is between cohesive materials of the same type or cohesive materials of different types. Examples of the bond properties which may vary are shear or peel resistance, pressure sensitivity of the bond, or other similar properties.

A wide variety of conventional cohesive materials are suitable for use in the present invention. Examples of webs of material which are both elastic and provided with cohesive properties are described in U.S. Pat. No. 6,156,424 issued to Taylor. It is generally desirable that the cohesive materials chosen do not increase their surface interaction over time and maintain their stability over the range of storage and use conditions typically seen by disposable absorbent articles of the type described herein. While it is recognized that most such cohesive materials will increase there surface interaction somewhat over time, it is desirable that this increase be minimized or at least remain within ranges suitable for the application. The cohesive materials may be supplied already disposed on the web material comprising the side portions, or it may be applied during manufacture of the garment as a whole. Other suitable cohesive materials may include latex, polyisoprene, polystyrene-polyisoprene-polystyrene or polystyrene-polybutadiene-polystyrene elastomers, budadiene-acrylonitrile-iosoprene or butadiene-acrylonitrile polymer materials. Materials such as poly(ethylene terephthalate), polyamide, polypropylene, or polyethylene based materials may also be used. These materials may be surface modified such as by chemical treatment, corona treatment or the like.

In addition to the features and properties previously described, any of the embodiments or variants of the present invention may be provided with additional optional features or characteristics. For example, pant like garments of the present invention may use cohesive areas (or other attachment mechanisms) to form a post use disposal means for the product. An example of such post use disposal means using mechanical fasteners is described in U.S. Pat. No. 4,963,140 to Robertson. It will be readily appreciated by one of skill in the art that the principles and techniques of the present invention using cohesive attachment methods can be employed to also create such a disposal means.

The side portion of garments of the present invention may also be provided with finger tabs or other means to assist in opening the side portion attachment area. This facilitates easy opening and refastening of the garment during use.

The side portions of garments of the present invention may be provided in a variety of colors and/or designs. For example, it may be desired to provide one color scheme for garments for boys and another color scheme for garments for girls. Additionally the color of the side portions (or other area of the garments) can be used to indicate which stage in a multi stage of development line up the product corresponds to.

The side portions can be provided with aids or indicia which facilitate refastenable closing of the product. For example, the side portions can have a size scale inscribed on one or both sides so that users may readily reattach the side portions together at the same location as previous attachments, or may know they desire to select a different attachment location which can be more readily found. Graphics and colors in the side portions can be used to indicate proper attachment. For example, the cohesive materials and corresponding side portions can be configured such that composite graphics or colors change upon opening and reattachment events indicating to the user the state of the garments' configuration.

Automatic registration techniques can be used to register the cohesive materials on the side portions of each garment during high speed manufacturing operations. This registration can be accomplished through the use of a reference character or mark on a suitable portion of the garment.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable pant like garment comprising:
a main absorbent portion comprising a liquid permeable topsheet, a liquid impermeable backsheet, and an absorbent core disposed therebetween, the main absorbent portion having a first waist region, a second waist region and a crotch region between and connecting the first and the second waist regions, the main absorbent portion having a first longitudinal edge and a second longitudinal edge;
a first side portion connected with the first waist region of the main absorbent portion and having a distal portion extending transversely outward from the first longitudinal edge of the main absorbent portion, the first side portion having a garment facing surface and an opposing body facing surface, the first side portion comprising a first cohesive engaging area defined by a cohesive substance disposed on the body facing surface and a second cohesive engaging area defined by a cohesive substance disposed on the garment facing surface of the distal portion;
a second side portion connected with the first waist region of the main absorbent portion and having a distal portion extending transversely outward from the second longitudinal edge of the main absorbent portion, the second side portion having a garment facing surface and an opposing body facing surface, the second side portion comprising a first cohesive engaging area defined by a cohesive substance disposed on the body facing surface and a second cohesive engaging area defined by a cohesive substance disposed on the garment facing surface of the distal portion;
a third side portion connected with the second waist region of the main absorbent portion and having a distal portion extending transversely outward from the first longitudinal edge of the main absorbent portion, the third side portion having a garment facing surface and an opposing body facing surface, the third side portion comprising a first cohesive receiving area defined by a cohesive substance disposed on the body facing surface and a second cohesive receiving area defined by a cohesive substance disposed on the garment facing surface of the distal portion;

a fourth side portion connected with the second waist region of the main absorbent portion and having a distal portion extending transversely outward from the second longitudinal edge of the main absorbent portion, the fourth side portion having a garment facing surface and an opposing body facing surface, the third side portion comprising a first cohesive receiving area defined by a cohesive substance disposed on the body facing surface and a second cohesive receiving area defined by a cohesive substance disposed on the garment facing surface of the distal portion;

a first frangible bond connecting the distal portion of the first side portion with the distal portion of the third side portion in an abutting facing relationship such that the first cohesive engaging area of the first side portion is directly facing and engaged with the first cohesive receiving area on the body facing surface opposite the second cohesive receiving area of the third side portion, wherein upon breaking the first frangible bond, the first cohesive engaging area of the first side portion may be refastenably joined with the second cohesive receiving area of the third side portion;

a second frangible bond connecting the distal portion of the second side portion with the distal portion of the fourth side portion in an abutting facing relationship such that the first cohesive engaging area of the second side portion is directly facing and engaged with first cohesive receiving area on the body facing surface opposite the second cohesive receiving area of the fourth side portion, wherein upon breaking the second frangible bond, the first cohesive engaging area of the second side portion may be refastenably joined with the second cohesive receiving area of the fourth side portion; and wherein the cohesive engaging and receiving areas do not include hook and loop fasteners.

2. The disposable pant like garment of claim 1, wherein the garment is packaged with the garment in a closed configuration.

3. The disposable pant like garment of claim 1, wherein the cohesive substance of the cohesive engaging areas is the same as the cohesive substance of the cohesive receiving areas.

4. The disposable pant like garment of claim 1, wherein the cohesive substance of the cohesive engaging areas is different from the cohesive substance of the cohesive receiving areas.

5. The disposable pant like garment of claim 1, wherein the first and second frangible bonds are thermal bonds.

6. The disposable pant like garment of claim 1, wherein the first and second frangible bonds are pressure bonds.

7. The disposable pant like garment of claim 1, wherein the first waist region is a front waist region, and the second waist region is a rear waist region.

8. The disposable pant like garment of claim 1, wherein each cohesive engaging area is coterminous with the first and second side portions, and wherein each cohesive receiving area is coterminous with the third and fourth side portions.

9. The disposable pant like garment of claim 1, wherein the cohesive engaging areas and the cohesive receiving areas are extensible.

* * * * *